United States Patent [19]

Bruzzese et al.

[11] Patent Number: 5,298,495
[45] Date of Patent: Mar. 29, 1994

[54] PARTRICIN DERIVATIVES

[75] Inventors: Tiberio Bruzzese; Massino Signorini, both of Milan; Franco Ottoni, Pieve Emanuele, all of Italy

[73] Assignee: SPA Societa' Prodotti Antibiotici SpA, Milan, Italy

[21] Appl. No.: 801,253

[22] Filed: Dec. 3, 1991

[30] Foreign Application Priority Data

Dec. 3, 1990 [IT] Italy .............................. 22268 A/90

[51] Int. Cl.⁵ ...................... A61K 31/70; C07H 17/08
[52] U.S. Cl. ......................................... 514/31; 536/6.5
[58] Field of Search .......................... 536/6.5; 574/31

[56] References Cited

U.S. PATENT DOCUMENTS 3,961,047  6/1976  Bruzzese et al. .................... 424/121
4,783,527 11/1988  Falkowski et al. .................. 536/53

FOREIGN PATENT DOCUMENTS 0428440 5/1991 European Pat. Off. .
0431870 6/1991 European Pat. Off. .
0431874 6/1991 European Pat. Off. .
0434943 7/1991 European Pat. Off. .

OTHER PUBLICATIONS

J. J. Kim Wright et al., N-Aminoacyl Derivatives of Polyene Macrolide Antibiotics and their Esters, vol. 35, No. 7, Journal of Antibiotics, Jul. 1982, pp. 911-914, Tokyo, JP.

R. C. Tweit, Characterization of the Antifungal and Antiprotozoal Antibiotic Partricin and Structural Studies on Partricins A and B, vol. 35, No. 8, Journal of Antibiotics, Aug. 1982, pp. 997-1005, Tokyo, JP.

J. Golik et al., The Structure of Mepartricin A and Mepartricin B, vol. 33, No. 8, Aug. 1980, pp. 904-907, Tokyo, JP.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

Derivatives of partricin and of its individual components, partricin A and B, wherein the mycosamine primary amino group forms an amide bond with the carboxy group of acids containing in addition a basic nitrogen group, the carboxy group at C-18 of macrolide ring being either free or in form of ester or neutral amide or containing in the chain a basic nitrogen moiety, their pharmaceutically acceptable salts, a process for preparing the same and pharmaceutical formulations containing the same.

12 Claims, No Drawings

PARTRICIN DERIVATIVES

DESCRIPTION

The present invention concerns derivatives of partricin and of its components, partricin A and B, their pharmaceutically acceptable salts, a process for preparing the same and pharmaceutical formulations containing the same.

Partricin is a polyene macrolide of the heptaene group. Its structure is reported in Merck Index, 11 Ed., No. 6997. It was isolated from fermentative broths of Streptomyces aureofaciens, NRRL 3878 strain (GB-B-1 357 538), and consists of two components in a ratio of about 1:1, partricin A and partricin B, the only difference between them being a group —$NHCH_3$ or —$NH_2$, respectively, in para position of the aromatic ring at the side chain bound to C-37 of macrolide. The two components are separated according to conventional methods, such as, for example, preparative silica gel or reversed phase chromatography or Craig countercurrent distribution; alternatively, the components A and B can be obtained independently by fermentation.

Partricin and its individual components A and B possess high antifungal and anti-protozoal activities. More recent studies have shown their potentiality also as anti-hypercholesterolemic, anti-hyperlipemic or antiviral agents and as therapeutic agents for curing the prostate benign hypertrophy. The pharmacological properties of partricin are to be ascribed to its bond and interaction capabilities with sterol compounds. However, owing to partricin high toxicity substantially due to its uncapability of discriminating between fungal cell wall ergosterol and human cell cholesterol, no practical application has been so far found for partricin in the therapeutic field.

On the contrary, its methyl ester or mepartricin (see, e.g. , U.S. Pat. No. -A-3,780,173 and Merck Index, 11 Ed., No. 5733), is widely used as an antifungal agent in topical and systemic formulations, and advantageously employed also in the treatment of prostate benign hypertrophy.

However, although this less toxic and more active derivative represents a substantial improvement as compared to partricin, mepartricin still possesses a rather high toxicity, and is likely to give rise to emolysis and nephrotoxicity, especially on long-term treatments.

Moreover, being mepartricin water-insoluble, the injectable solutions required for the treatment of serious systemic infections can be prepared only in the presence of surfacting agents, such as, for example, sodium lauryl sulfate (SLS). It must be appreciated, however, that this technique does not allow true solutions to be obtained, but only micellar dispersions, as indicated by both absorption maxima characteristically shifted to longer wavelengths and varied absorbance in UV spectra. It must also be taken into account that the presence of a surfacting agent, such as SLS, in the formulations can cause additional toxicity.

In consequence of the foregoing, and notwithstanding the presence of a number of functional groups in the molecule of partricin hindering univocal chemical transformations, a real request still exists of novel derivatives, which:

a) possess lower toxicity and higher activity as compared to the natural antibiotic and mepartricin, b) can be transformed, by means of pharmaceutically acceptable agents, into water-soluble salts, suitable for preparing injectable forms and oral formulations endowed with better bioavailability.

The object of the present invention is to provide derivatives of partricin and of its individual components A and B of the following general formula (I):

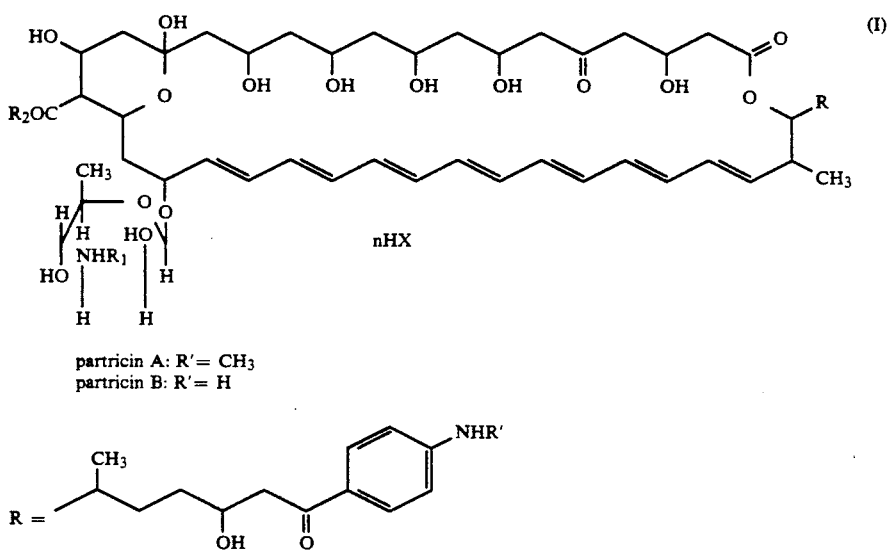

partricin A: R' = $CH_3$
partricin B: R' = H wherein

R' is a hydrogen atom (partricin B) or a methyl group (partricin A) $R_1$ represents an aminoacyl radical —$CO(CH_2)_m NR_3 R_4$, wherein m = 1, 2 or 3, $R_3$ and $R_4$, which can be the same or different, represent a hydrogen atom or a $C_1$–$C_3$ alkyl group or form with the nitrogen atom to which they are bound, a five- or six-membered heterocyclic ring optionally containing another hetero atom selected from O, S and N, this latter being preferably methyl- or 2-hydroxyethyl-substituted;

$R_2$ represents a hydroxy, $C_1$–$C_6$ alkoxy, $NR_3 R_4$ amino or —NH—$(CH_2)_m$——$NR_3 R_4$ aminoalkylamino group, wherein m, $R_3$ and $R_4$ have the same meaning as above, or a substituted —NH—$(CH_2)_m$—$R_5$ alkylamino group, wherein m has the same meaning as above and R₅ represents a five- or six-membered nitrogen heterocyclic ring, optionally N-methyl- or N-ethyl - substituted.

X represents the anion of a pharmaceutically acceptable, organic or inorganic acid, and n is 0, 1 or 2.

From the foregoing it follows that the present derivatives are basic amides at the mycosamine amino group of partricin A and B or of their ester or amide derivatives at the C-18 carboxy group. The mycosamine amino group is therefore transformed into an amide derivative by reaction with the carboxy group of an acid containing a primary, secondary or tertiary amino group, in order to maintain a basic site in said molecular position. The C-18 carboxy group is either free or, alternatively, modified by formation of derivatives, such as esters or neutral or basic amides.

Starting materials for the synthesis of the derivatives of the present invention are partricin, partricin A and B and their derivatives at the carboxy group, such as, for example, esters (U.S. Pat. No. -A-3,780,173) and amides. These latter can he easily synthesized by reacting the C-18 carboxy group with a primary or secondary amine, in the presence of diphenylphosphorazidate. The synthesis of the present derivatives involves the formation of an amide bond between the primary amino group at C-3' in the above starting materials (hereinafter only "amines") and the carboxy group of an amino acid of general formula (II):

HOOC—(CH₂)$_m$—NR₃R₄ wherein m, R₃ and R₄ have the above indicated meanings. The preparation is carried out according to methods known in the field of chemical syntheses, such as, for example, the reaction between the amine and the acid chloride, preferably in the presence of an HCl acceptor, such as an inorganic or tertiary organic base; the reaction between the amine and an ester of the amino acid; the direct reaction between the amino and carboxy groups by means of dicyclohexylcarbodiimide (DCCD), in the presence of not of adjuvants, such as, for example, 4-dimethylaminopyridine (DMAP) or 1-hydroxybenzotriazole (HOBT); the reaction between the amine and an amino acid carboxy-activated derivative, such as, for example, hydroxysuccinimide ester, esters with mono-, dinitro- or polyhalophenols, the imidazolide prepared by reaction with carbonyldiimidazole or the azide formed in situ with diphenylphosphorazidate (DPPA), optionally in the presence of tertiary organic bases; such as, for example, triethylamine.

Especially advantageous is the use of DPPA; the starting amine derivative is dissolved in a mixture of chlorinated solvents and lower aliphatic alcohols or, preferably, in polar aprotic solvents, such as, for example, dimethylformamide, dimethylacetamide, dimethyl sulfoxide, etc. and then treated with equimolar amounts of DPPA and acid. The molar ratio of DPPA/acid to amine is in the range of 1 to 6, and the addition of reagents to amine is carried out either all at once or by slow dropping or portionwise, at appropriate intervals. The reaction times are in the range of 1 to 36 hours, preferably 3 to 12 hours. The temperature is in the range of 0° to 50° C., usually 15° to 25° C.

The optimum conditions for preparing each individual product are selected according to preliminary experiments, the progress of the reaction being controlled by thin layer chromatography (TLC). When the reaction has been completed or an optimum ratio of the product to unreacted amine or by-products, if any, is achieved, as indicated by TLC, the reaction products are precipitated by suitable organic solvents and filtered off.

The final purification is carried out according to various techniques, such as, for example, by dissolution and reprecipitation in solvents, crystallization, chromatography and Craig countercurrent distribution.

Chromatrography and countercurrent distribution also allow the present partricin derivatives to be separated into the individual components A and B. These latter however, are preferably obtained according to the above described methods by using as starting materials the individual components of partricin A and B, their esters and amides.

Alternatively, the present derivatives wherein the C-18 carboxy group is in form of ester or amide, are obtained by the already described condensation reaction of the primary amino (mycosamino) group of partricin A or B with amino acids of general formula (II), followed by the preparation of esters or amides at the carboxy group, according to the above-mentioned methods.

The derivatives of the present invention are solids of deep yellow color, high and ill-defined melting point (gradual decomposition), soluble in polar aprotic solvents, such as dimethylsulfoxide, dimethylformamide, dimethylacetamide, etc, poorly soluble in the most common organic solvents insoluble in water. The final control and characterization of the final products are carried out by the usual techniques: TLC, HPLC, elemental analysis, mass spectrometry, IR, UV. As far as UV spectra are concerned, it should be considered that the spectra of present derivatives and corresponding starting materials are qualitatively the same, because the chromophore is unchanged.

The derivatives of the present invention are transformed into salts by reaction with pharmaceutically acceptable, inorganic or organic acids, such as, for example, hydrochloric, sulfuric, benzoic, glycolic, gluconic, glucuronic, ascorbic, aspartic, glutamic acid, etc.

Said salts are obtained by adding 1-2 moles of acid to the aqueous suspension of the present derivatives. From the resulting solutions the salts are isolated according to usual methods, such as, for example, vacuum evaporation to dryness, freeze-drying, spray-drying, concentration and cooling, precipitation by water-miscible organic solvents, etc. Salts with organic acids are preferred because their aqueous solutions are usually neutral or only weakly acidic. The above-mentioned salts are enough soluble in water so as injectable pharmaceutical forms can be prepared. Moreover, the bioavailability of oral pharmaceutical forms, prepared with active ingredients in form of water-soluble salts, is usually higher.

The derivatives of the present invention show anti-fungal and anti-protozoal activities comparable with, or even higher than, partricin and mepartricin, but lower both haemolytic power and local and systemic toxicity.

Those properties result in a more favourable therapeutic index, whereby these compounds are useful not only for the clinical therapy of fungal and protozoal infections, but also, and especially, for the treatment of diseases requiring long-term treatments, such as, for example, hypercholesterolemia, hyperlipemia, prostate benign hypertrophy, etc. The lower toxicity of the present derivatives and of their salts also allows their utilization at high dosage rate.

For all therapeutic uses, the derivatives of the present invention and their salts can be diluted with appropriate amounts of a pharmaceutically acceptable, liquid or solid carrier. Formulations include, for example, tablets, effervescent tablets, powders, granules, capsules for oral administration as well as suspensions and solutions in suitable aqueous and oily carriers for oral administration. Slow-release oral forms and enteric-coated formulations are also produced. These latter are particularly suitable for obviating the reduced stability of some of the present derivatives in a medium at strongly acidic pH.

Creams and ointments are prepared for use in dermatology and suppositories, bougies and vaginal suppositories or tablets for topical use.

The present derivatives can be administered also parenterally in form of aqueous sterile solutions or, preferably, as freeze-dried powders dissolved at the time of usage. In the injectable formulations, even more than in other formulations, the compounds are employed in form of water-soluble salts.

In case of necessity, combinations with other drugs are possible, depending on the pathological conditions to be subjected to the therapeutic treatment.

The following examples are intended to illustrate the invention, but are not to be taken as limiting the scope thereof.

The partricin derivatives described in the following examples have been checked by IR and UV spectrometry, elemental analysis, thin layer chromatography (TLC) and high-pressure liquid chromatography (HPLC).

TLC was carried out on Silica gel 60, F254 Merck, plates using a $CH_2Cl_2/MeOH/H_2O/NH_4OH$, 85/15/1/1 v/v, mixture as eluant, and UV lamp, $\lambda=254$ nm, as detector.

HPLCs were carried out on an Hitachi-Merck instrument, consisting of L 6200 ternary gradient pump, L 4000 UV variable wavelenght detector and L 2000 integrator.

Conditions: Merck Hibar Lichrocart 125 mm, $\phi 4$ mm, Column packed with Superspher 100 RP-18,4 μm; mixtures of 5 mM EDTA in $H_2O$ and acetonitrile as eluant; detection: UV, $\lambda=378$ nm; flow rate 1 ml/mm; room temperature. The following three types of gradient were used:

|  | % EDTA | % Acetonitrile |
|---|---|---|
| Gradient A | | |
| t = 0 | 65 | 35 |
| t = 10' | 65 | 35 |
| t = 25' | 55 | 45 |
| t = 35' | 55 | 45 |
| *t = 36' | 65 | 35 |
| *t = 46' | 65 | 35 |
| Gradient B | | |
| t = 0 | 65 | 35 |
| t = 35' | 60 | 40 |
| t = 55' | 60 | 40 |
| *t = 56' | 65 | 35 |
| *t = 66' | 65 | 35 |
| Gradient C | | |
| t = 0 | 67 | 33 |
| t = 30' | 60 | 40 |
| t = 50' | 58 | 42 |
| *t = 51' | 67 | 33 |

|  | % EDTA | % Acetonitrile |
|---|---|---|
| *t = 61' | 67 | 33 |

*back to the starting conditions and re-equilibration of the column

EXAMPLE 1

N-dimethylaminoacetyl-partricin A, methyl ester 11.4 g (10 mmoles) of partricin A methyl ester (mepartricin A) were dissolved in 110 ml of dimethylacetamide. To this solution 5.15 g (50 mmoles) of dimethylaminoacetic acid (dimethylglycine), 5.05 g (50 mmoles) of triethylamine and 13.76 g (50 mmoles) of diphenylphosphorazidate were successively added under stirring and at room temperature. The solution was kept for 6 hours under stirring at room temperature its progress being checked by TLC (the procedure is detailed in the introduction to the examples). The reaction mixture was then treated with 1 l of ether/ethanol mixture (9:1), the precipitate was filtered off, washed with ether and dried under vacuum at 40° C. The resulting raw product (about 12 g) was purified preferably by medium-pressure preparative chromatography (MPLC) using silica gel in a weight ratio of 12:1 to the raw product. A $CH_2Cl_2/CH_3OH/H_2O/NH_4OH$ mixture, 85/15/1/1 v/v, was used as eluant. Alternatively, the raw product could be purified by Craig countercurrent distribution or column chromatography with silica gel, with the same eluant mixture used for MPLC.

The MPLC fractions, pure according to TLC, are pooled and evaporated to dryness under vacuum. 7 g of pure product are obtained in form of a deep yellow crystalline powder.

TLC: Rf = 0.52

HPLC: retention time = 26.21' (gradient A)

Elem. analysis for $C_{64}H_{95}N_3O_{20}$ found: C 62.51%, H 7.95%, N 3.36%.

calc.: C 62.67%, H 7.81%, N 3.43%.

EXAMPLE 2

N-DIMETHYLAMINOACETYL-PARTRICIN B METHYL ESTER

The title product was prepared according to the procedure of Example 1, starting from mepartricin B.

The product was in form of a deep yellow crystalline powder.

TLC: Rf = 0.23

HPLC: Retention time = 19.32' (gradient A)

Elem. analysis for $C_{63}H_{93}N_3O_{20}$ found: C 62.30%, H 7.79%, N 3.39%.

calc.: C 62.41%, H 7.73%, N 3.47%.

EXAMPLE 3

N-DIMETHYLAMINOACETYL-PARTRICIN METHYL ESTER

The title product was prepared according to the procedure of Example 1, starting from mepartricin as A + B complex in a ratio of about 1:1.

TLC: Rf = 0.52 (component A) and 0.23 (component B)

HPLC: Retention time = 26.21' (A) and 19.32' (B) (gradient A)

EXAMPLE 4

The derivatives listed in the following Table 1 with their respective HPLC retention times and TLC Rf values were prepared by reacting the mycosamine amino group of the corresponding ester or amide derivatives at the carboxy group of partricin or partricin A and B with amino acids, such as 1-piperidine-propionic acid, 4-methyl-1-piperazine-acetic acid, 4-(2-hydroxyethyl)-l-acetic acid, dimethylaminoacetic acid in the presence of triethylamine and diqhenylphosphorazidate. Reaction conditions (temperature, molar ratios between partricin derivatives and reagents) and procedure were essentially the same as those of Example 1.

The optimum reaction times for each preparation were determined by means of preliminarly reactions of 5 mmoles of starting derivatives of partricin, the reaction being stopped when the most favourable ratio of the conversion to final product to the formation of impurities and by-products was achieved. In each instance the times were in the range of between 4 and 8 hours.

The so obtained derivatives, after purification by column chromatography with silica gel, were all in form of yellow crystalline powders and showed satisfactory C, H, N data of the elemental analysis.

A few data on microbiological activity on C.albicans, on hemolytic activity and acute toxicity in mice are reported in Table 2.

TABELLA I $$P\begin{matrix}\nearrow NHR_1 \\ \searrow COR_2\end{matrix} \qquad (I)$$

| P | $R_1$ | $R_2$ | HPLC (Retention time) (min.) | Syst. HPLC | TLC (Rf) |
|---|---|---|---|---|---|
| Partr. A | $-COCH_2-N(CH_3)_2$ | $-NH-CH_2CH_2-N(CH_3)_2$ | 25.16 | B | 0.25 |
| Partr. A | $-COCH_2-N(CH_3)_2$ | $-NH-CH_2-$(N-ethyl-pyrrolidinyl) | 22.25 | A | 0.14 |
| Partr. A | $-COCH_2-N(CH_3)_2$ | $-N$(piperazinyl)$N-CH_2CH_2-OH$ | 21.31 | B | 0.27 |
| Partr. A | $-COCH_2-N(CH_3)_2$ | $-N$(piperazinyl)$N-CH_3$ | 19.68 | A | 0.40 |
| Partr. A | $-COCH_2-CH_2-N$(piperidinyl) | $-OCH_3$ | 29.69 | A | 0.44 |
| Partr. A | $-COCH_2-CH_2-N$(piperidinyl) | $-NH-CH_2CH_2-N(CH_3)_2$ | 28.74 | A | 0.26 |
| Partr. A | $-COCH_2-CH_2-N$(piperidinyl) | $-NH-CH_2-$(N-ethyl-pyrrolidinyl) | 24.42 | A | 0.11 |
| Partr. A | $-COCH_2-CH_2-N$(piperidinyl) | $-N$(piperazinyl)$N-CH_2CH_2-OH$ | 26.23 | B | 0.26 |
| Partr. A | $-COCH_2-CH_2-N$(piperidinyl) | $-N$(piperazinyl)$N-CH_3$ | 20.27 | A | 0.34 |

TABELLA I-continued $$P{\overset{NHR_1}{\underset{COR_2}{\diagdown}}} \quad (I)$$

| P | R₁ | R₂ | HPLC (Retention time) (min.) | Syst. HPLC | TLC (Rf) |
|---|---|---|---|---|---|
| Partr. A | —COCH₂—N(C₄H₈)N—CH₃ | —OCH₃ | 34.40 | C | 0.31 |
| Partr. A | —COCH₂—N(C₄H₈)N—CH₃ | —NH—CH₂CH₂—N(CH₃)₂ | 10.76 | A | 0.12 |
| Partr. A | —COCH₂—N(C₄H₈)N—CH₃ | —N(C₄H₈)N—CH₂CH₂—OH | 21.16 | B | 0.11 |
| Partr. A | —COCH₂—N(C₄H₈)N—CH₃ | —N(C₄H₈)N—CH₃ | 8.66 | B | 0.18 |
| Partr. A | —COCH₂—N(C₄H₈)N—CH₂CH₂—OH | —OCH₃ | 32.72 | C | 0.27 |
| Partr. A | —COCH₂—N(C₄H₈)N—CH₂CH₂—OH | —NH—CH₂CH₂—N(CH₃)₂ | 21.84 | A | 0.09 |
| Partr. A | —COCH₂—N(C₄H₈)N—CH₂CH₂—OH | —N(C₄H₈)N—CH₂CH₂—OH | 20.48 | A | 0.075 |
| Partr. A | —COCH₂—N(C₄H₈)N—CH₂CH₂—OH | —N(C₄H₈)N—CH₃ | 21.52 | B | 0.13 |
| Partr. A | —COCH₂—N(CH₃)₂ | —NH—CH₂CH₂CH₂N(CH₃)₂ | 26.20 | B | 0.23 |
| Partr. A | —COCH₂—N(CH₃)₂ | —NH—CH₂CH₂—(2-pyridyl) | 32.44 | B | 0.39 |
| Partr. A | —COCH₂CH₂N(C₅H₁₀) | —NH—CH₂—CH₂—(2-pyridyl) | 26.65 | B | 0.34 |
| Partr. B | —COCH₂—N(CH₃)₂ | —NH—CH₂CH₂N(CH₃)₂ | 18.66 | B | 0.14 |
| Partricina | —COCH₂—N(CH₃)₂ | —NH—CH₂CH₂N(CH₃)₂ | {18.66, 25.16} | B | {0.14, 0.25} |

TABELLA 2

$$\text{P} \diagup^{\text{NHR}_1}_{\diagdown \text{COR}_2} \quad (I)$$

| P | R₁ | R₂ |
|---|----|----|
| Partr. A | —COCH₂—N(CH₃)₂ | —NH—CH₂CH₂—N(CH₃)₂ |
| Partr. A | —COCH₂—N(CH₃)₂ | —N(piperazinyl)N—CH₂CH₂—OH |
| Partr. A | —COCH₂—N(CH₃)₂ | —N(piperazinyl)N—CH₃ |
| Partr. A | —COCH₂—CH₂—N(piperidinyl) | —OCH₃ |
| Partr. A | —COCH₂—CH₂—N(piperidinyl) | —NH—CH₂CH₂—N(CH₃)₂ |
| Partr. A | —COCH₂—CH₂—N(piperidinyl) | —N(piperazinyl)N—CH₂CH₂—OH |
| Partr. A | —COCH₂—CH₂—N(piperidinyl) | —N(piperazinyl)N—CH₃ |
| Partr. A | —COCH₂—N(piperazinyl)N—CH₃ | —OCH₃ |
| Partr. A | —COCH₂—N(piperazinyl)N—CH₃ | —NH—CH₂CH₂—N(CH₃)₂ |
| Partr. A | —COCH₂—N(piperazinyl)N—CH₃ | —N(piperazinyl)N—CH₂CH₂—OH |
| Partr. A | —COCH₂—N(piperazinyl)N—CH₃ | —N(piperazinyl)N—CH₃ |
| Partr. A | —COCH₂—N(piperazinyl)N—CH₂CH₂—OH | —OCH₃ |
| Partr. A | —COCH₂—N(piperazinyl)N—CH₂CH₂—OH | —NH—CH₂CH₂—N(CH₃)₂ |

TABELLA 2-continued $$\underset{COR_2}{\overset{NHR_1}{P<}} \quad (I)$$

| Partr. A | $-COCH_2-N\overset{\frown}{\underset{\smile}{\phantom{X}}}N-CH_2CH_2-OH$ | $-N\overset{\frown}{\underset{\smile}{\phantom{X}}}N-CH_2CH_2-OH$ |

Partr. A    $-COCH_2-N\overset{\frown}{\underset{\smile}{\phantom{X}}}N-CH_2CH_2-OH$    $-N\overset{\frown}{\underset{\smile}{\phantom{X}}}N-CH_3$ Partr. A    $-COCH_2-N(CH_3)_2$        $-NH-CH_2CH_2CH_2N(CH_3)_2$ Partr. A    $-COCH_2-N(CH_3)_2$        $-NH-CH_2CH_2-\text{(2-pyridyl)}$ Partr. A    $-COCH_2CH_2-N\overset{\frown}{\underset{\smile}{\phantom{X}}}$    $-NH-CH_2-CH_2-\text{(2-pyridyl)}$

| Partr. | H | OH |
| Partr. | H | OCH₃ |

| P | MIC (ng/ml) C. albicans 73 Fluid Sab. Med. 36° C. | | Hemolytic con.(mcg/ml) rat erytrocytes, 4 h at 37° C. | | DL50 (mg/kg) mice |
|---|---|---|---|---|---|
| | 24 h | 48 h | total (THC) | min.(MHC) | |
| Partr. A | 7.5 | 15 | >18 | 18 | 158(i.p.), 58 (i.v.) |
| Partr. A | 7.5 | 21.2 | 0.7 | 0.2 | — |
| Partr. A | 7.5 | 21.2 | 2 | 0.2 | 3.6 (i.p.) |
| Partr. A | 7.5 | 42.4 | 18 | 3.5 | >30 (i.p.) |
| Partr. A | 7.5 | 30 | 18 | 6 | 43.6 (i.p.) |
| Partr. A | 7.5 | 30 | 2 | 0.2 | — |
| Partr. A | 7.5 | 15 | 3.5 | 0.2 | — |
| Partr. A | 15 | 30 | 18 | 0.7 | 29.3 (i.p.) |
| Partr. A | 10.6 | 30 | 18 | 2 | >100 (i.p.) |
| Partr. A | 15 | 21.2 | 2 | 0.2 | — |
| Partr. A | 7.5 | 21.2 | 0.7 | 0.2 | 3.8 (i.p.) |
| Partr. A | 15 | 30 | 18 | 0.7 | >30 (i.p.) |
| Partr. A | 7.5 | 21.2 | 18 | 0.7 | >100 (i.p.) |
| Partr. A | 10.6 | 21.2 | 0.7 | 0.2 | — |
| Partr. A | 7.5 | 15 | 0.7 | 0.2 | — |
| Partr. A | 15 | 30 | 10.4 | 0.2 | 12.4 (i.p.) |
| Partr. A | 15 | 42.4 | >18 | 18 | >300 (i.p.), 76.8(i.v.) |
| Partr. A | 30 | 60 | >18 | 6 | >300 (i.p.), 109 (i.v.) |
| Partr. | 30 | 60 | <0.2 | <0.2 | 0.63 (i.p.) |
| Partr. | 7.5 | 30 | 18 | 0.7 | 15.8 (i.p.), 5.02(i.v.) |

EXAMPLE 5

N-DIMETHYLAMINOACETYL-PARTRICIN A 2-DIMETHYL-AMINOETHYLAMIDE DIASPARTATE 1,28 g of N-dimethylaminoacetyl-partricin A 2-dimethylaminoethylamide, prepared as described in Example 4, and 0,27 g of aspartic acid acid were added to 30 ml of distilled water and the resulting suspension was kept under stirring over a few minutes till total dissolution.

The resulting yellow solution was evaporated under vacuum to dryness, the residue slurried with a little amount of ethanol, filtered and dried at 40° C. under vacuum. The salt was a yellow crystalline powder, soluble in water with almost neutral reaction (pH 6), having the same TLC (Rf =0.25) and HPLC (retention time =25.16′, gradient B) characteristics of the free base.

Elem. analysis for $C_{75}H_{117}N_7O_{27}$ found: C 57.99%, H 7.44%, N 6.19%.

calc.: C 58.16%, H 7.61%, N 6.33%.

Alternatively, the diaspartate compound was isolated from the aqueous solution, prepared as above, according to the following techniques:

a) freeze-drying b) spray-drying c) concentration under vacuum to half volume and precipitation by addition of about 12 volumes of ethanol or acetone.

Whichever the isolation procedure may be, the salt showed in every instance satisfactory analytical data (C,H,N elemental analysis, TLC, HPLC).

EXAMPLE 6

According to the procedure described in the previous Example, the following salts were prepared from the corresponding free bases described in Example 4.

The salts showed the same TLC and HPLC characteristics of the free bases (see the Rf and retention time data reported in Table 1).

N-dimethylaminoacetyl partricin A - 2-dimethylamino ethylamide diglutamate

Elem. analysis: for $C_{77}H_{121}N_7O_{27}$ found % C 58.72, H 7.69, N 6.25.
calc. % C 58.65, H 7.74, N 6.22.

N-dimethylaminoacetyl partricin A - 2-dimethylaminoethylamide digluconate

Elem. analysis: for $C_{79}H_{127}H_5O_{33}$ found % C 56.72, H 7.55, N 4.14.
calc. % C 56.65, H 7.64, N 4.18.

N-dimethylaminoacetyl partricin A - /4-(2-hydroxyethyl)/piperazide diaspartate

Elem. analysis: for $C_{77}H_{119}N_7O_{25}$ found % C 58.02, H 7.48, N 6.18.
calc. % C 58.13, H 7.54, N 6.16.

N-dimethylaminoacetyl partricin A - (4-methyl)piperazide diglycolate

Elem. analysis: for $C_{72}H_{111}N_5O_{25}$ found % C 59.85, H 7.69, N 4.87.
calc. % C 59.77, H 7.73, N 4.84.

N-dimethylaminoacetyl partricin A (4-methyl)piperazide diglucuronate

Elem. analysis: for $C_{80}H_{123}N_5O_{33}$ found % C 57.15, H 7.31, N 4.20.
calc. % C 57.09, H 7.37, N 4.16.

N-dimethylaminoacetyl partricin A - (4-methyl)piperazide diascorbate

Elem. analysis for: $C_{80}H_{119}N_5O_{31}$ found % C 58.35, H 7.31, N. 4.29.
calc. % C 58.34, H 7.28, N. 4.25.

N-piperidinopropionyl partricin A - (4-methyl)piperazide diaspartate

Elem. analysis for: $C_{80}H_{123}N_7O_{27}$ found % C 59.54, H 7.62, N 6.1.
calc. % C 59.48, H 7.68, N 6.07.

N-4-methylpiperazinoacetyl partricin A - 2-dimethylamino ethylamide diaspartate

Elem. analysis for: $C_{78}H_{122}N_8O_{27}$ found % C 58.52, H 7.71, N 6.93.
calc. % C 58.41, H 7.67, N 6.99.

N-4-(2-hydroxyethyl)piperazinoacetyl partricin A - 2-dimethylamino ethylamide diaspartate Elem. analysis for: $C_{79}H_{124}N_8O_{28}$ found % C 57.99, H 7.73, N 6.83.
calc. % C 58.07, H 7.65, N 6.86.

We claim:

1. A compound of the formula (I):

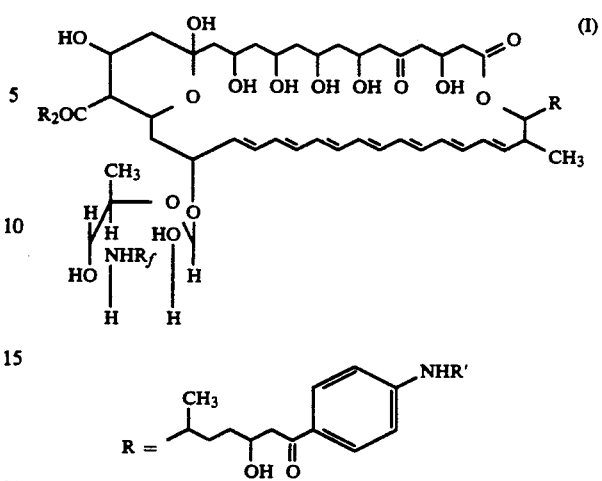

wherein
R' is a hydrogen atom or a methyl group;
$R_1$ represents a $-CO(CH_2)_m NR_3R_4$ aminoacyl radical, wherein m=1, 2 or 3, $R_3$ and $R_4$ which can be the same or different, represent a $C_1$-$C_3$ alkyl group or together form with the nitrogen atom to which they are bound, a five or six-membered heterocyclic ring that may contain an additional nitrogen atom substituted by a methyl or 2-hydroxyethyl group;
$R_2$ represents an $-NR_3R_4$ amino or $-NH-(CH_2)_m-NR_3R_4$ aminoalkylamino group, wherein m is 1, 2 or 3, $R_3$ and $R_4$ independently are $C_1$-$C_3$ alkyl group or together form a heterocyclic ring as defined above, or an $-NH-(CH_2)_m-R_5$ alkylamino group, wherein m has the same meaning as above and $R_5$ represents a five-or six-membered heterocyclic ring wherein the hetero atom is nitrogen substituted by methyl or ethyl;
X represents the anion of a pharmaceutically acceptable, organic or inorganic acid, and n i 0, 1 or 2.

2. The compound according to claim 1, wherein the additional hetero atom of the $NR_3R_4$ heterocycle is selected from the group consisting of methyl substituted nitrogen and 2-hydroxyethyl-substituted nitrogen.

3. Compound according to claim 1, wherein $R_1$ is selected from the group consisting of:

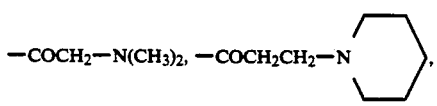

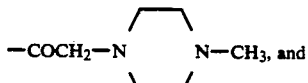

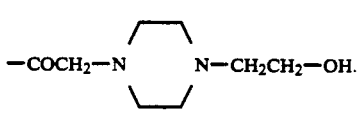

4. Compound according to claim 1, wherein $R_2$ is a member of the group consisting of:

-continued

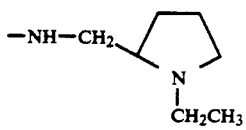

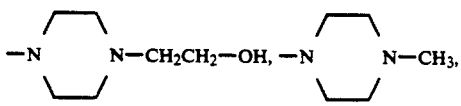

and

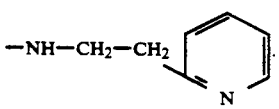

5. Compound according to claim 1 wherein X is selected from the group consisting of the anion of aspartic, glutamic, glycolic, glucuronic, gluconic, and ascorbic acid.

6. Compound according to claim 1, which is N-dimethylaminoacetyl-partricin A dimethylamino-ethylamide or a pharmaceutically acceptable salt thereof.

7. Compound according to claim 1, which is N-dimethylaminoacetyl-partricin A dimethylaminoethylamide diaspartate.

8. Compound according to claim 1, which is N-(4-methyl-1-piperazinoacetyl)partricin A 2-dimethylaminoethylamide or a pharmaceutically acceptable salt thereof.

9. Compound according to claim 1, which is N-(4-hydroxyethyl-1-piperazinoacetyl)partricin A 2-dimethylaminoethylamide or a pharmaceutically acceptable salt thereof.

10. Compound according to claim 1, which is N-dimethylaminoacetyl-partricin A 2-pyridylethyl amide or a pharmaceutically acceptable salt thereof.

11. Compound according to claim 1, which is N-piperidinopropionyl-partricin A 2-pyridylethyl amide or a pharmaceutically acceptable salt thereof.

12. Pharmaceutical formulations having activity against fungal and Protoza infections, hypercholesterolemic and hyperlipemic conditions, and prostate benign hypertrophy, containing a therapeutically effective amount of a compound of formula (I) according to claim 1, in combination with a pharmaceutically acceptable excipient.

* * * * *

UNITED STATES PATENT AND TRADEMARK OFFICE
CERTIFICATE OF CORRECTION

PATENT NO. : 5,298,495
DATED : March 29, 1994
INVENTOR(S) : Tiberio BRUZZESE, et al.

It is certified that error appears in the above-indentified patent and that said Letters Patent is hereby corrected as shown below:

On the title page, Item [75], the 2nd inventor's first name should read as follows:

--Massimo--

Signed and Sealed this

Twenty-sixth Day of July, 1994

Attest:

BRUCE LEHMAN

Attesting Officer        Commissioner of Patents and Trademarks

UNITED STATES PATENT AND TRADEMARK OFFICE
CERTIFICATE OF CORRECTION

Page 1 of 4

PATENT NO. : 5,298,495
DATED : MARCH 29, 1994
INVENTOR(S) : Tiberio BRUZZESE, ET AL.

It is certified that error appears in the above-identified patent and that said Letters Patent is hereby corrected as shown below:

Columns 1 and 2, line 40,

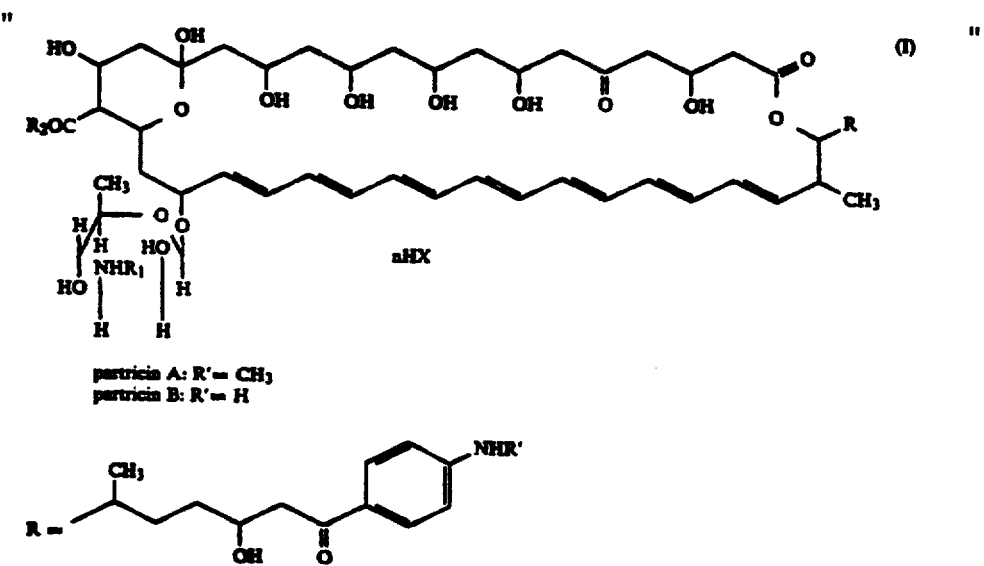

UNITED STATES PATENT AND TRADEMARK OFFICE
CERTIFICATE OF CORRECTION

PATENT NO. : 5,298,495
DATED : MARCH 29, 1994
INVENTOR(S) : Tiberio BRUZZESE, ET AL.

It is certified that error appears in the above-identified patent and that said Letters Patent is hereby corrected as shown below:

should read:

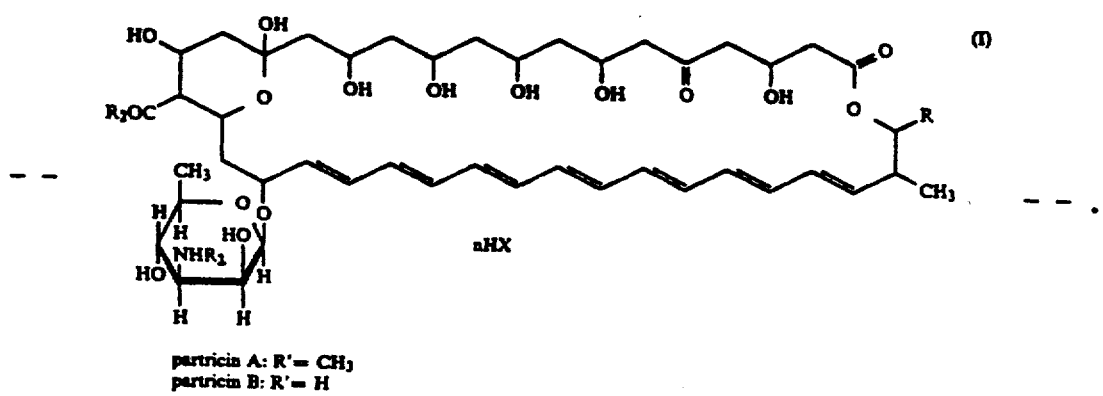

partricin A: R'= CH₃
partricin B: R'= H

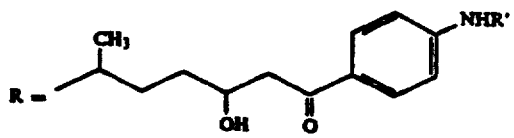

UNITED STATES PATENT AND TRADEMARK OFFICE
CERTIFICATE OF CORRECTION

PATENT NO. : 5,298,495
DATED : MARCH 29, 1994
INVENTOR(S) : Tiberio BRUZZESE, ET AL.

It is certified that error appears in the above-identified patent and that said Letters Patent is hereby corrected as shown below:

Column 16, line 1,

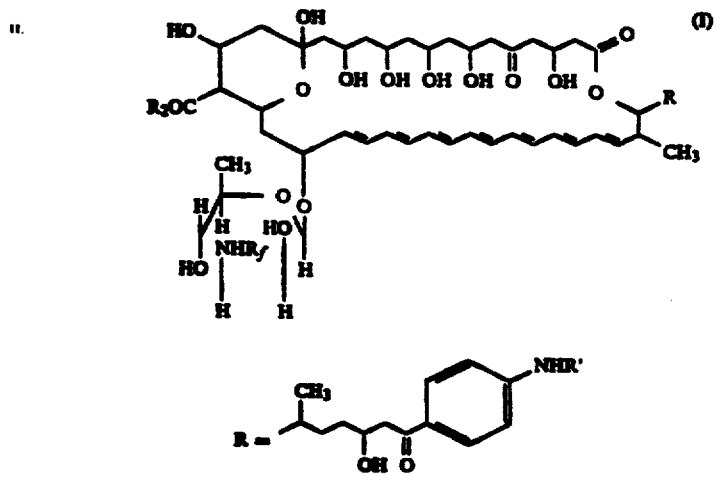

UNITED STATES PATENT AND TRADEMARK OFFICE
CERTIFICATE OF CORRECTION

PATENT NO. : 5,298,495
DATED : MARCH 29, 1994
INVENTOR(S) : Tiberio BRUZZESE, ET AL.

Page 4 of 4

It is certified that error appears in the above-identified patent and that said Letters Patent is hereby corrected as shown below:

should read:

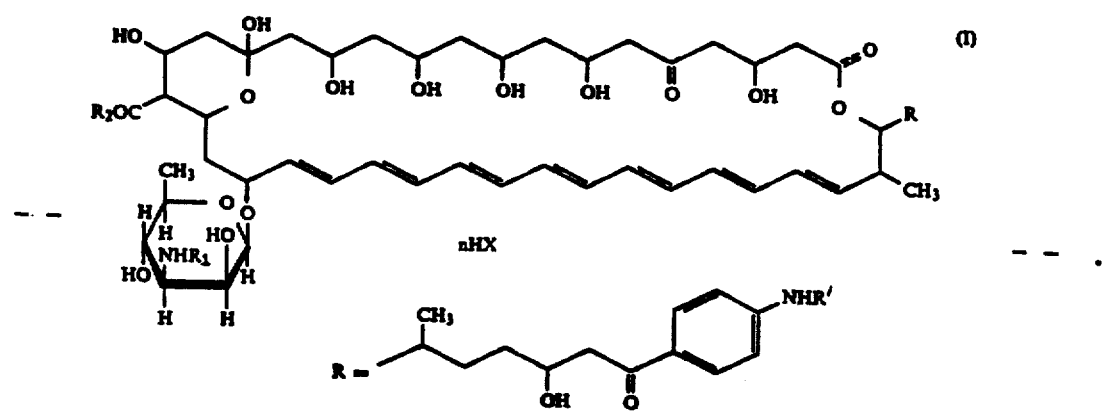

Signed and Sealed this

Second Day of December, 1997

Attest:

BRUCE LEHMAN

Attesting Officer

Commissioner of Patents and Trademarks